(12) United States Patent
Augustine (10) Patent No.: US 10,098,659 B2
(45) Date of Patent: Oct. 16, 2018

(54) TUNNELER DEVICE INCLUDING A SEPARATION PREVENTION DEVICE

(71) Applicant: Covidien LP, Mansfield, MA (US)

(72) Inventor: James Augustine, Bridgewater, MA (US)

(73) Assignee: Covidien LP, Mansfield, MA (US)

( * ) Notice: Subject to any disclaimer, the term of this patent is extended or adjusted under 35 U.S.C. 154(b) by 1078 days.

(21) Appl. No.: 13/625,253

(22) Filed: Sep. 24, 2012

(65) Prior Publication Data

US 2014/0088564 A1    Mar. 27, 2014

(51) Int. Cl.
A61B 17/34        (2006.01)
A61M 25/01       (2006.01)
A61B 17/32        (2006.01)

(52) U.S. Cl.
CPC ..... *A61B 17/3415* (2013.01); *A61M 25/0194* (2013.01); *A61B 2017/320056* (2013.01)

(58) Field of Classification Search
CPC ... A61B 2017/320056; A61B 17/3415; A61M 25/0194; A61M 25/0067; A61M 39/10
See application file for complete search history.

(56) References Cited

U.S. PATENT DOCUMENTS

| 4,098,028 | A | * | 7/1978 | Prunier | B24B 13/005 451/390 |
| 4,705,041 | A | | 11/1987 | Kim | |
| 4,832,687 | A | * | 5/1989 | Smith, III | A61M 25/06 604/274 |
| 5,637,102 | A | * | 6/1997 | Tolkoff | A61M 39/12 285/417 |
| 5,944,732 | A | * | 8/1999 | Raulerson et al. | 606/167 |
| 6,423,053 | B1 | * | 7/2002 | Lee | A61M 39/1011 604/523 |
| 6,453,185 | B1 | | 9/2002 | O'Keefe | |
| 7,128,734 | B1 | * | 10/2006 | Wilson | A61B 17/3415 403/311 |
| 8,574,192 | B2 | * | 11/2013 | Haarala | A61B 17/3415 604/104 |

(Continued)

FOREIGN PATENT DOCUMENTS

WO    WO 2005/009502 A2    2/2005

OTHER PUBLICATIONS

Plastics, General Survey, 1. Definition, Molecular Structure and Properties. Ullman's Encyclopedia of Industrial Chemistry. Elias et al. Published online Apr. 2015.*

*Primary Examiner* — Bhisma Mehta
*Assistant Examiner* — Matthew A Engel
(74) *Attorney, Agent, or Firm* — Kenneth Collier; Jessica Kwak Rauckman (57) ABSTRACT

A tunneler device is provided which includes a handle, a shaft extending distally from the handle, a connecting device including a body supported on a distal end of the shaft configured to be received within a lumen of a catheter, and a resilient separation prevention device supported on the connecting device. The resilient separation prevention device is inwardly deflectable towards the connecting device upon insertion of the connection device into the lumen of the catheter and biased towards a non-deflected position in engagement with an inner surface of the catheter to prevent retraction of the connecting device from the catheter.

18 Claims, 7 Drawing Sheets

(56) References Cited

U.S. PATENT DOCUMENTS

| | | | |
|---|---|---|---|
| 8,708,897 B2* | 4/2014 | Braga | A61B 17/32 600/184 |
| 8,979,744 B2* | 3/2015 | Braga et al. | 600/184 |
| 9,381,036 B2* | 7/2016 | Rome | A61B 17/3415 |
| 2004/0034324 A1* | 2/2004 | Seese | A61M 1/285 604/246 |
| 2004/0176739 A1 | 9/2004 | Stephens et al. | |
| 2004/0230204 A1 | 11/2004 | Wortley et al. | |
| 2005/0027282 A1* | 2/2005 | Schweikert et al. | 604/523 |
| 2005/0209584 A1* | 9/2005 | Rome | A61M 25/0097 604/536 |
| 2006/0009783 A1* | 1/2006 | Rome | A61B 17/3415 606/108 |
| 2006/0015130 A1 | 1/2006 | Voorhees, Jr. et al. | |
| 2006/0095062 A1* | 5/2006 | Stephens | A61B 17/3415 606/191 |
| 2006/0135949 A1* | 6/2006 | Rome | A61B 17/3415 604/533 |
| 2007/0049960 A1 | 3/2007 | Stephens et al. | |
| 2007/0078396 A1* | 4/2007 | Feeley | A61B 17/3415 604/164.01 |
| 2007/0265597 A1 | 11/2007 | Schweikert et al. | |
| 2007/0282274 A1* | 12/2007 | Chesnin | 604/175 |
| 2008/0086161 A1 | 4/2008 | Massengale et al. | |
| 2008/0097409 A1* | 4/2008 | Stephens | 604/533 |
| 2008/0214992 A1* | 9/2008 | Haarala | A61B 17/3415 604/44 |
| 2009/0137944 A1* | 5/2009 | Haarala et al. | 604/44 |
| 2010/0063513 A1* | 3/2010 | Braga | A61B 17/32 606/108 |
| 2014/0088564 A1* | 3/2014 | Augustine | 604/528 |
| 2016/0089180 A1* | 3/2016 | Entabi | A61B 17/3415 604/26 |

\* cited by examiner

TUNNELER DEVICE INCLUDING A SEPARATION PREVENTION DEVICE

TECHNICAL FIELD

The present disclosure relates to indwelling catheter tunnelers and more particularly to a tunneler including a separation prevention device.

BACKGROUND

Catheters are flexible instruments which facilitate the withdrawal and introduction of fluids from and to body cavities, ducts, and vessels. Typically, a distal end of the catheter is implanted into, for example, the vasculature of a patient to withdraw blood from the patient or introduce medicaments into the patient. When a catheter is implanted into the vasculature of a patient, the catheter's distal portion is inserted through an incision in the patient's skin through an opening in the vasculature (venotomy site) until the distal tip is precisely located at a desired site. The proximal portion of the catheter remains external of the patient to provide access to the catheter for infusion and/or withdrawal of fluids such as for hemodialysis. Typically, the proximal portion of the catheter is directed away from the venotomy site to a remote site through a subcutaneous tunnel such that the catheter can be comfortably positioned on a patient's body for long term use. To accomplish this, a tunneler device is typically secured to the proximal portion of the catheter and the catheter is pulled by the tunneler device through the subcutaneous tunnel.

Tunneler devices have one end which is configured to securely engage the proximal end of the catheter. Typically, the engagement end of the tunneler device includes at least one extension segment which is dimensioned to be received within a lumen or lumens of the catheter. Although this provides somewhat effective connection of the tunneler device to the catheter, detachments are known to occur during a subsequent tunneling procedure. Such detachments require additional steps and therefore increase the duration of the catheter placement procedure, and may also lead to introduction of air into the catheter.

It would be beneficial to have a tunneling device including a catheter securement device which is capable of improved securement of the tunneler device to the catheter to prevent detachment during a tunneling procedure.

SUMMARY

Accordingly, a tunneler device is provided. In general, in one aspect of the present disclosure, a tunneler device includes a handle, a shaft extending distally from the handle, a connecting device including a body supported on a distal end of the shaft configured to be received within a lumen of a catheter, and a resilient separation prevention device.

In various embodiments, the resilient separation prevention device is supported on the connecting device and is configured to be deflected inwardly towards the connecting device during insertion of the connecting device into the lumen of the catheter to facilitate insertion of the connecting device into the catheter and urged towards a non-deflected position in engagement with the lumen of the catheter to prevent separation of the tunneler device and the catheter. The separation prevention device may be formed of a substantially rigid material to facilitate movement of the separation prevention device relative to the connecting device while providing resiliency to urge the separation prevention device away from the connecting device. The separation prevention device includes a fixed end supported on a distal end of the connecting device and a free end. The free end deflects inwardly towards the connecting device during insertion of the connecting device into the lumen of the catheter and is urged towards the non-deflected position. The separation prevention device is biased away from the connecting device when deflected inwardly towards the connecting device. In certain embodiments, the separation prevention device may be substantially cone shaped.

In various embodiments, the tunneler device further includes a cap that is selectively engageable with the connecting device. The body of the connecting device may include a threaded segment with an external thread and the cap may include an internal thread such that the internal thread of the cap and the external thread of the threaded segment of the body are selectively threadably enagageable to secure the cap to the connecting device.

According to another aspect of the present disclosure, a tunneler device includes a handle, a shaft extending distally from the handle, a connecting device including a body supported on a distal end of the shaft configured to be received within a lumen of a catheter, and a resilient separation prevention device supported on the connecting device. The resilient separation prevention device is inwardly deflectable towards the connecting device upon insertion of the connection device into the lumen of the catheter and urged towards a non-deflected position in engagement with an inner surface of the catheter to prevent retraction of the connecting device of the tunneler device from the catheter.

In certain embodiments, the separation prevention device is formed of a substantially rigid material to facilitate movement of the separation prevention device relative to the connecting device while providing resiliency to urge the separation prevention device away from the connecting device. The separation prevention device includes a fixed end supported adjacent to a distal end of the connecting device and a free end. The free end deflects inwardly towards the connecting position during insertion of the connecting device into the lumen of the catheter and is urged towards the non-deflected position. The separation prevention device is biased toward the non-deflected position when deflected inwardly towards the connecting device. In various embodiments, the separation prevention device is substantially cone shaped.

In certain embodiments, the tunneler device includes a cap that is selectively engageable with the connecting device to enclose the connecting device and the resilient separation prevention device. The body of the connecting device may include a threaded segment with an external thread and the cap may include an internal thread such that the internal thread of the cap and the external thread of the threaded segment of the body are selectively threadably enagageable to secure the cap to the connecting device.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

The embodiments of the present disclosure are directed to a tunneling system including a catheter and a tunneling device for properly positioning the catheter within a patient. The tunneling system of the present disclosure may have various medical applications. For example, during a hemodialysis catheter implantation procedure, the tunneling device may be manipulated by a clinician to create or enlarge a subcutaneous tunnel within a patient to properly position the catheter on the patient. It is envisioned that the presently disclosed tunneling system may be employed in any other suitable procedure.

As used herein, the term "clinician" refers to a doctor, a nurse, or any other care provider and may include support personnel. The term "proximal" refers to the portion of a structure that is closer to a clinician, whereas the term "distal" refers to the portion of a structure that is farther from the clinician.

Figure 1:
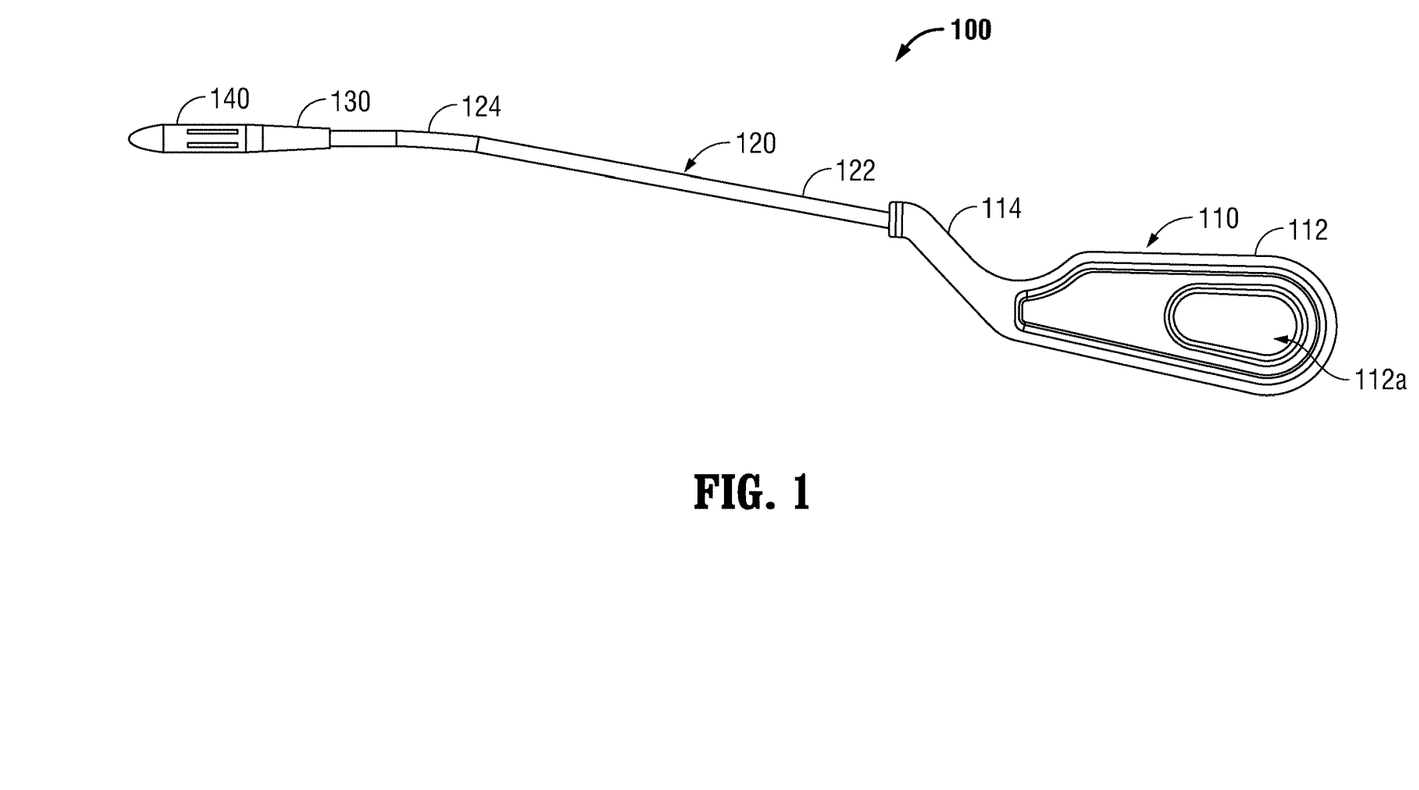
FIG. 1 is a side view of a tunneler device according to the present disclosure.

With reference to FIG. 1, a tunneler device according to the present disclosure is shown generally as tunneler device 100. Although tunneler device 100 will be described for use in the placement of a dialysis catheter within a patient, tunneler device 100 may be used for the placement of various other medical implements. Tunneler device 100 includes a handle 110, a shaft 120 extending from handle 110, a connecting device 130 mounted on a distal end of shaft 120, and a tunneling cap 140 selectively engageable with connecting device 130. Any or all of the components of tunneler device 100 may be sterilizable, and thus, reusable. Alternatively, tunneler device 100 may be disposable.

With continuing reference to FIG. 1, handle 110 is supported on a proximal end of tunneler device 100 and is configured for operable engagement by a clinician. In particular, handle 110 includes a loop 112 defining an opening 112a at a proximal end of handle 110 dimensioned to receive the clinician's fingers. A distal handle segment 114 is provided at a distal end of handle 110 that supports a proximal end of shaft 120. Distal handle segment 114 is obliquely arranged with respect to shaft 120 at any suitable angle to displace or offset the hand of the clinician relative to the patient during use in a tunneling procedure. Handle 110 may include ridges, bumps, knurls, and/or any other suitable non-slip features configured to facilitate gripping engagement by a clinician. Handle 110 may also be configured for operable engagement with a robotic arm (not shown) or other mechanical manipulating device.

A proximal end of shaft 120 is secured to, and may be embedded within, distal handle segment 114 of handle 110 to connect handle 110 and shaft 120 together. Shaft 120 extends distally from distal handle segment 114 and includes a proximal shaft segment 122 and a distal shaft segment 124. In one embodiment, handle 110 is molded about a proximal end of proximal shaft segment 122 of shaft 120. Alternatively, shaft 120, handle 110, and connecting device 130 can be unitarily formed. Distal shaft segment 124 is obliquely arranged with respect to proximal shaft segment 122 at any suitable angle to facilitate formation of a tunnel in a patient as desired. Further, shaft 120 may be malleable to enable the clinician to bend shaft 120 as needed for a particular procedure. For example, the clinician may bend shaft 120 into a curved shape to enable tunneler device 100 to create a curved or arced tunnel.

Figure 2:
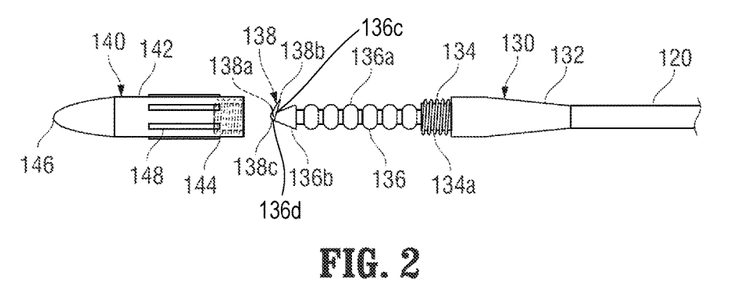
FIG. 2 is an enlarged side view, with parts separated, of a distal region of an embodiment of the presently disclosed tunneler device.
Figure 3:
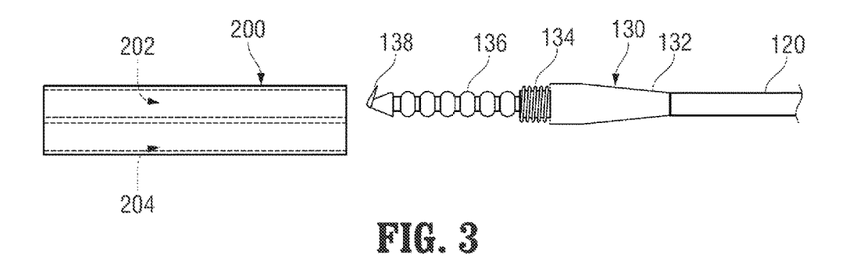
FIG. 3 is an enlarged side view of the distal region of the tunneler device of FIG. 2 with a proximal region of a catheter.
Figure 4:
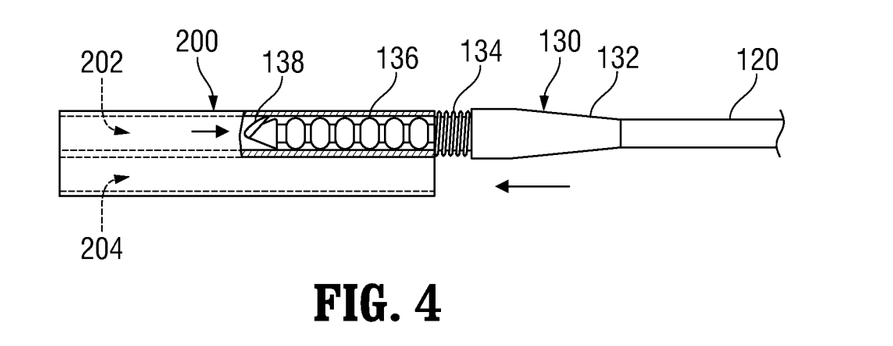
FIG. 4 is an enlarged side view of the distal region of the tunneler device of FIG. 2 being inserted within the proximal region of the catheter.
Figure 5:
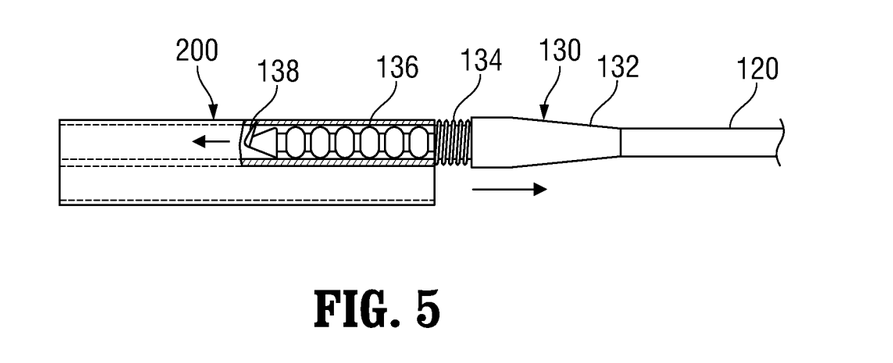
FIG. 5 is an enlarged side view of the distal region of the tunneler device of FIG. 4 being subjected to separation forces.

Turning now to FIG. 2, connecting device 130 is supported on the distal end of shaft 120 and may include a main body 132 for supporting connecting device 130 on the distal end of shaft 120, a threaded segment 134 for engaging cap 140, and an extension segment 136 for engaging a catheter 200 (with one or more lumens) (see FIGS. 3-5). A separation prevention device 138 for retaining the catheter 200 on the extension segment 136 is provided on or adjacent to a distal end of the extension segment 136. As appreciated, connecting device 130 may be integrally formed with shaft 120, or, in the alternative, secured to shaft 120 using known techniques such as overmolding.

With continuing reference to FIG. 2, the threaded segment 134 may include one or more external threads 134a adjacent the main body 132 that facilitate threaded engagement with one or more internal threads 144 of cap 140, discussed in greater detail below. The extension segment 136 may extend distally from threaded segment 134 and include a plurality of barbs 136a and a blunt tip 136b. The cap 140 is removed from the connecting device 130 to expose the extension segment 136. The extension segment 136 is dimensioned to be received within a lumen 202, 204 of the catheter 200 such that the barbs 136a frictionally engage an inner surface of the catheter 200 to secure the extension segment 136 to the catheter 200.

As best depicted in FIGS. 2-5, separation prevention device 138 may include a resilient body 138a that may be formed, such as by machining or stamping, into any suitable shape including, for example, a disk or cone shape, or portion thereof. The body 138a of the separation prevention device 138 is supported on the extension segment 136 in a cantilevered arrangement and has a first end (or free end) 138b and a second end (or fixed end) 138c (FIG. 2). The first end 138b extends to a proximal edge that is free and movable while the second end 138c is fixedly secured to, or adjacent to, a distal tip 136d of a distal end 136c of a blunt tip 136b of the extension segment 136. The first end 138b is positioned proximally of the second end 138c such that body 138a defines a downwardly sloped surface towards the distal end of extension segment 136. As shown in FIG. 4, when the extension segment 136 is inserted into one of the lumens 202, 204 of the catheter 200, the body 138a of the separation prevention device 138 engages an inner wall of the catheter 200 and is deflected towards the extension segment 136 to facilitate insertion of the extension segment 136 into a respective lumen 202, 204 of catheter 200. When inserted within a lumen 202 of catheter 200, as shown in FIG. 5, the first end 138b of the separation prevention device 138 is biased outwardly into contact with an inner surface of the catheter to a locked position. The separation prevention device 138 may be formed of a resilient, substantially rigid material which is normally positioned in the locked position. When the separation prevention device 138 is positioned within a lumen 202, 204 against the inner surface of the catheter 200, the separation prevention device may deflect inward towards the extension segment 136. The material and/or configuration of the separation prevention device 138 urges the separation prevention device 138 outward away from the extension segment 136 into engagement with the inner surface of the catheter 200. Any attempt to disengage the extension segment 136 from the catheter 200 will cause a proximal edge of the first end 138b of the separation prevention device 138 to dig into the inner surface of the catheter 200 by being urged to expanding outwardly, thereby preventing separation of the tunneler device 100 from the catheter 200.

Figure 2A:
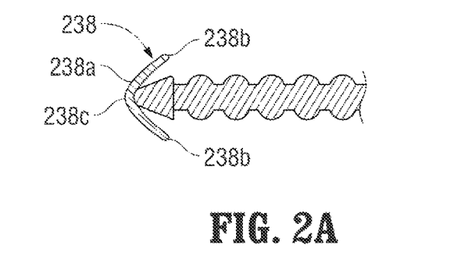
FIG. 2A is an enlarged side view of a distal region of another embodiment the presently disclosed tunneler device.

As discussed above, although the separation prevention device 138 is shown as a resilient finger or disk, other configurations are envisioned which would enable entry into a lumen of a catheter, but, due to the resilient nature and angular orientation of the separation prevention device 138, would prevent withdrawal of the separation prevention device 138 from a lumen of a catheter. For example, as illustrated in FIG. 2A, another embodiment of a separation prevention device 238 includes a body 238a that has a substantially conical configuration. Separation prevention device 238 includes a first end 238b that extends to a free proximal edge and a second end 238c. Similar to separation prevention device 138, the proximal edge of the first end 238b of separation prevention device 238 digs into the inner surface of a catheter 200 to prevent separation of the tunneler device 100 from the catheter 200 when separation forces are applied to the catheter 200 and the tunneler device 100.

Figure 6:
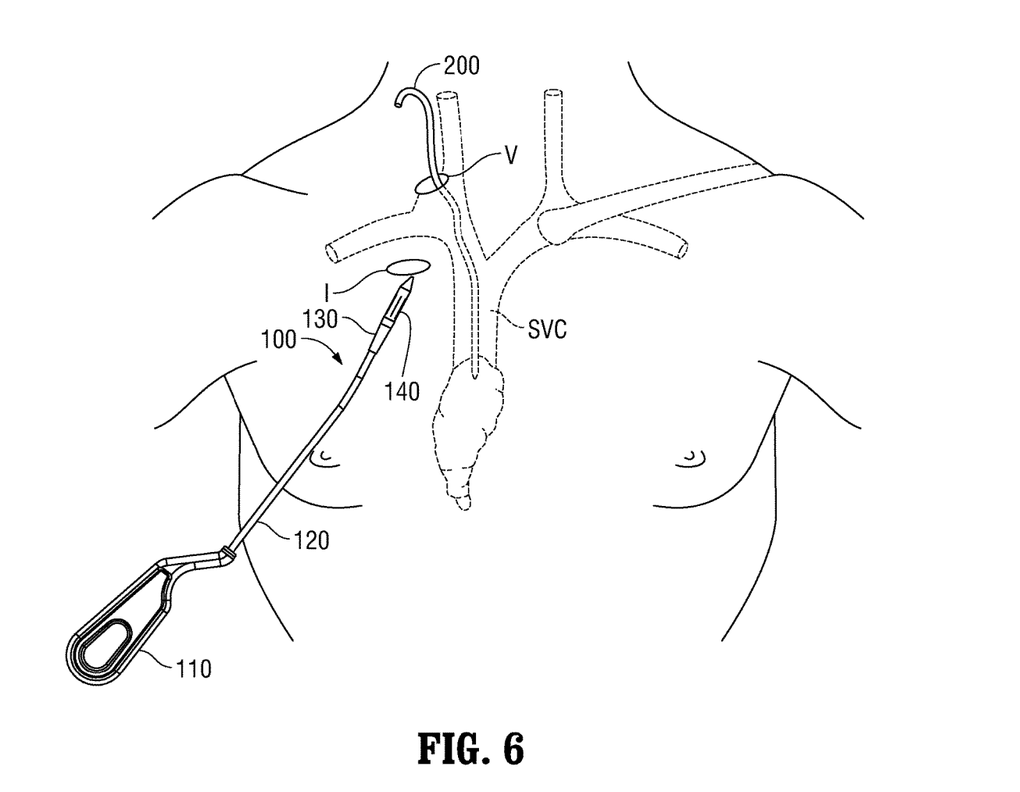
FIGS. 6-9 are progressive views illustrating a tunneling procedure utilizing the presently disclosed tunneler device.
Figure 7:
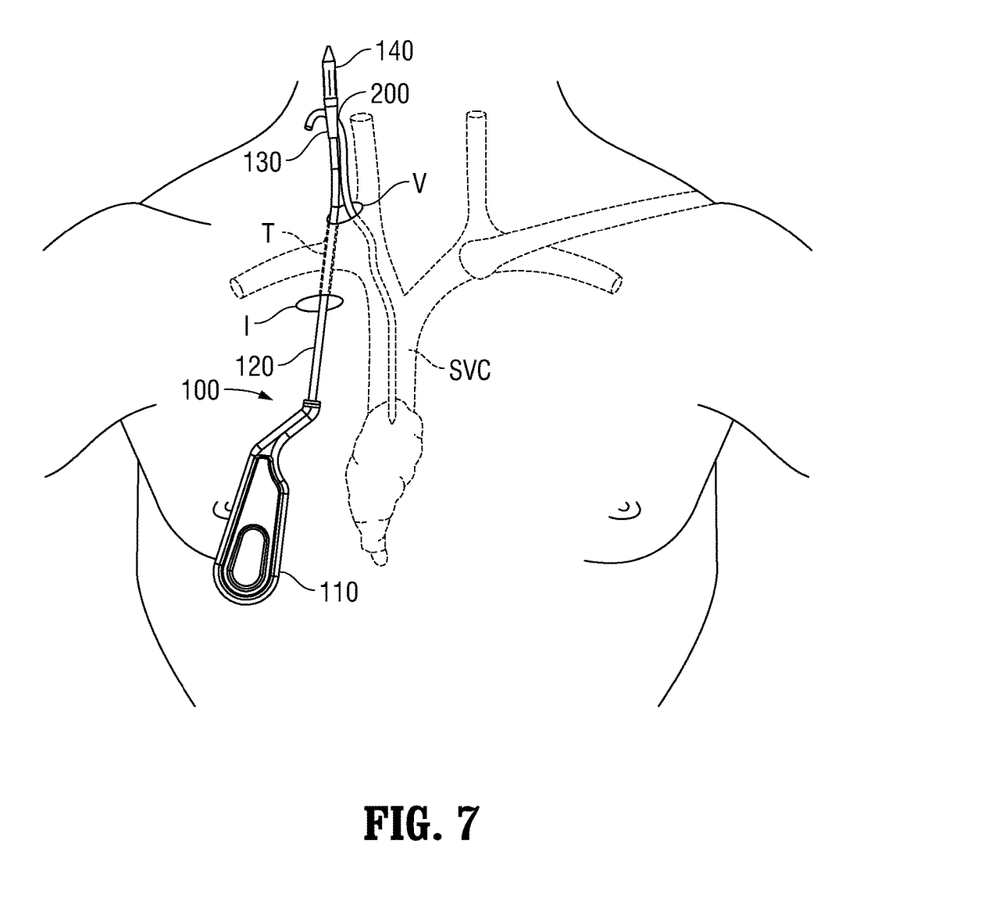

Again with regard to FIG. 2, the tunneling cap 140, which may operate as a tissue dissector or expander, includes a substantially bullet-shaped body 142 that facilitates passage of the tunneler device 100 through subcutaneous tissue during a tunneling procedure (see FIG. 6). The body 142 includes internal threads 144 at a proximal end and a substantially rounded atraumatic tip 146 at a distal end. As discussed above, the internal threads 144 of the body 142 mate with the external threads 134a of the threaded segment 134 of the connecting device 130 to releasably secure the cap 140 to the connecting device 130. With the tunneling cap 140 secured to the connecting device 130, the extension segment 136 is enclosed within the cap 140 to facilitate passage of the tunneler device 100 through the subcutaneous tissue. Although the cap 140 and the connecting device 130 are shown configured for threaded engagement with each other by virtue of the threaded segment 134, any suitable arrangement may be utilized to releasably the secure cap 140 to the connecting device 130. For example, the cap 140 may be secured to the connecting device 130 with a bayonet coupling or via friction fit arrangement. The cap 140 may be provided in various sizes for creating tunnels of different sizes. In this manner, the tunneler device 100 may be used for the implantation of catheters having different sizes. The cap 140 may include longitudinal ribs 148 which extend along at least a portion of a length of substantially bullet-shaped body 142. The ribs 148 may be configured to facilitate manipulation of the cap 140 by a clinician during placement and removal of the cap 140 relative to the connecting device 130.

Referring to FIGS. 3-8, the use of the tunneler device 100 will now be described with respect to an exemplary procedure. In use, after catheter 200 has been positioned into a patient's vasculature, for example, the superior vena cava "SVC", such that a proximal end of the catheter 200 extends from the venotomy site "V" (FIG. 6), a subcutaneous tunnel "T" (FIG. 7) is formed between the venotomy site "V" and a position remote from the venotomy site "V". To accomplish this, an incision "I" is made at a desired position remote from the venotomy site "V" and the distal end of the tunneler device 100, with the cap 140 attached, is inserted through the incision "I" and pushed through the tissue to the venotomy site "V."

Figure 8:
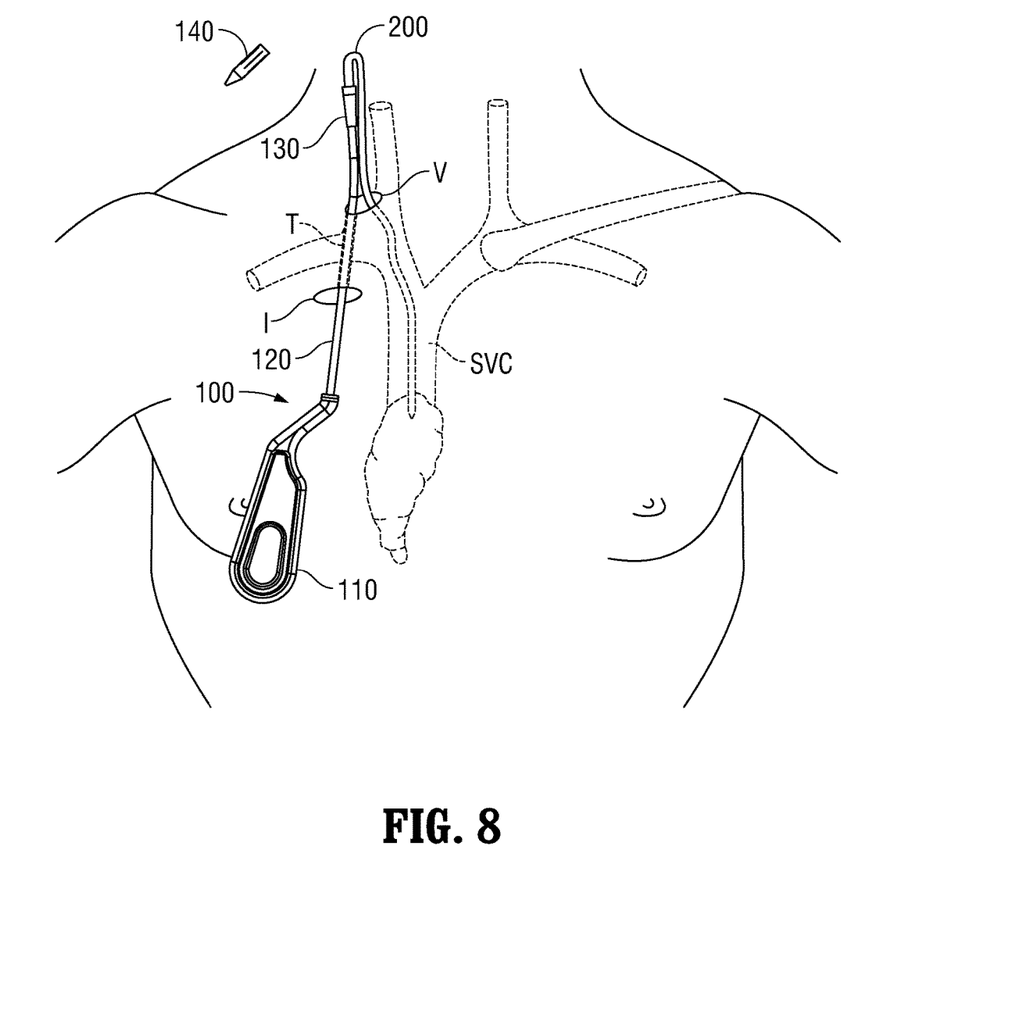

After the distal end of the tunneler 100 is positioned to extend from the venotomy site "V", the cap 140 is removed from the distal end of the tunneler device 100 to expose the connecting device 130 and the extension segment 136 of the connecting device 130 is inserted into one of the lumens 202, 204 at the proximal end of the catheter 200 (FIGS. 4 and 8). Alternatively, the connecting device 130 may include two extension segments (not shown) which are received in each of the lumens 202, 204 of the catheter 200. One or both of the extension segments may include a separation prevention device 138, 238. As the connecting device 130 is inserted into a lumen of the catheter 200, the separation prevention device 138, 238 engages the catheter 200 and is deformed such that end 138b, 238b of the separation prevention device 138, 238 is deformed downwardly towards extension segment 136, but is urged away from the extension segment 136 due to the resilient nature of the material or configuration of the separation prevention device. The plurality of barbs 136a and the end 138b, 238b of the separation prevention device 138, 238 of the connecting device 130 engage with the inner surface of the catheter 200 such that the separation prevention device 138, 238 is disposed in a locked position. In this position, any attempt to retract extension segment 136 from a lumen 202, 204 of the catheter 200 will cause the end 138b, 238b of the body 138a, 238a of the separation prevention device 138, 238 to dig into the inner surface of the catheter 200 to prevent separation of the tunneler device 100 from the catheter 200.

Figure 9:
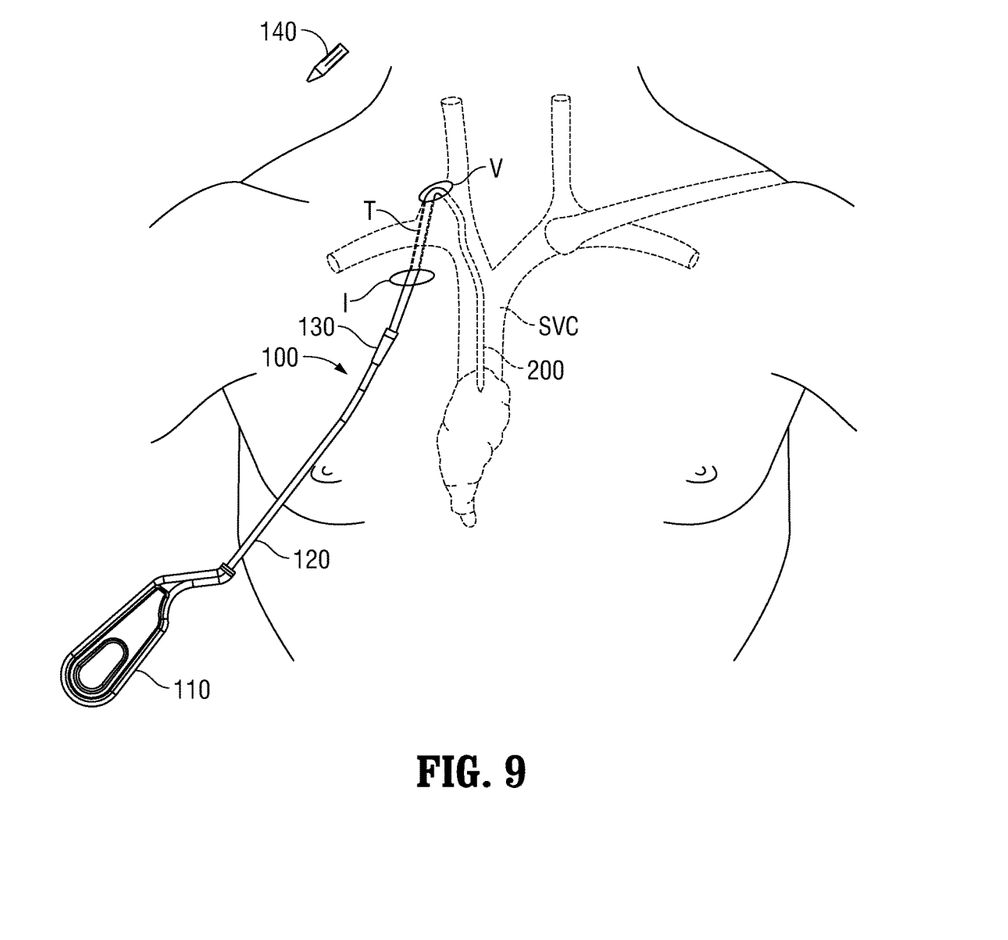

As best shown in FIGS. 8-9, once the catheter 200 is secured to the tunneler device 100 through the engagement of the connecting device 130 with the proximal end of the catheter 200, the tunneler device 100 is drawn back through tunnel "T" such that the proximal end of the catheter 200 is drawn through the tunnel "T" to extend outwardly from incision "I." The catheter 200 may then be disconnected from the tunneling device 100. In particular, the proximal end of the catheter 200 may be cut to disengage the tunneler device 100 from the rest of the catheter 200. As discussed above, any or all of the tunneler device 100 may be disposable or sterilizable and reusable.

As can be appreciated, the tunneler device of the present disclosure and any of its components may be formed of any suitable polymeric or metallic material and combinations thereof.

Persons skilled in the art will understand that the structures and methods specifically described herein and illustrated in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure.

Accordingly, the subject matter of the present disclosure is not to be limited by what has been particularly shown and described.

What is claimed is:

1. A tunneler device, comprising:
   a handle;
   a shaft extending distally from the handle;
   a connecting device including a body supported on a distal end of the shaft configured to be received within a lumen of a catheter; and
   a resilient separation prevention device supported on a distal end of the connecting device, wherein the resilient separation prevention device defines a free end, the resilient separation prevention device and the free end configured to be deflected inwardly towards the connecting device and towards the shaft during insertion of the connecting device into the lumen of the catheter to facilitate insertion of the connecting device into the catheter, and the free end configured to dig into an inner surface of the catheter defining the lumen to prevent separation of the connecting device and the catheter, wherein the resilient separation prevention device defines a fixed end fixedly secured at a distal tip of the distal end of the connecting device, the free end positioned proximally of the fixed end, and wherein the resilient separation prevention device defines a downwardly sloped surface towards the distal end of the connecting device, and the resilient separation prevention device configured to be urged towards a non-deflected position into engagement with the lumen of the catheter when the connecting device is within the lumen of the catheter.

2. The tunneler device of claim 1, further comprising a cap that is selectively engageable with the connecting device.

3. The tunneler device of claim 2, wherein the body of the connecting device includes a threaded segment with an external thread and the cap includes an internal thread such that the internal thread of the cap and the external thread of the threaded segment of the body are selectively threadably enageageable to secure the cap to the connecting device.

4. The tunneler device of claim 1, wherein the resilient separation prevention device is formed of a substantially rigid material configured to facilitate movement of the resilient separation prevention device relative to the connecting device while providing resiliency to urge the resilient separation prevention device away from the connecting device.

5. The tunneler device of claim 4, wherein the free end is urged to the non-deflected position when the connecting device is within the lumen of the catheter.

6. The tunneler device of claim 1, wherein the resilient separation prevention device is substantially cone shaped.

7. The tunneler device of claim 1, wherein the resilient separation prevention device is biased away from the connecting device when deflected inwardly towards the connecting device.

8. The tunneler device of claim 1, wherein the free end of the resilient separation prevention device is biased outwardly from the connecting device when the connecting device is within the lumen of the catheter.

9. The tunneler device of claim 1, wherein the body of the connecting device defines a solid interior.

10. A tunneler device, comprising:
    a handle;
    a shaft extending distally from the handle;
    a connecting device including a body supported on a distal end of the shaft configured to be received within a lumen of a catheter; and
    a resilient separation prevention device supported on a distal end of the connecting device, wherein the resilient separation prevention device defines a free end, the resilient separation prevention device and the free end inwardly deflectable towards the connecting device and towards the shaft upon insertion of the connecting device into the lumen of the catheter, and the free end diggable into an inner surface of the catheter defining the lumen to prevent separation of the connecting device and the catheter, wherein the resilient separation prevention device defines a fixed end fixedly secured at a distal tip of the distal end of the connecting device, the free end positioned proximally of the fixed end, and wherein the resilient separation prevention device defines a downwardly sloped surface towards the distal end of the connecting device, and the resilient separation prevention device urged towards a non-deflected position into engagement with the inner surface of the catheter when the connecting device is within the lumen of the catheter.

11. The tunneler device of claim 10, further comprising a cap that is selectively engageable with the connecting device to enclose the connecting device and the resilient separation prevention device.

12. The tunneler device of claim 11, wherein the body of the connecting device includes a threaded segment with an external thread and the cap includes an internal thread such that the internal thread of the cap and the external thread of the threaded segment of the body are selectively threadably enageageable to secure the cap to the connecting device.

13. The tunneler device of claim 10, wherein the resilient separation prevention device is formed of a substantially rigid material configured to facilitate movement of the resilient separation prevention device relative to the connecting device while providing resiliency to urge the resilient separation prevention device away from the connecting device.

14. The tunneler device of claim 13, wherein the free end is urged towards the non-deflected position when the connecting device is within the lumen of the catheter.

15. The tunneler device of claim 10, wherein the resilient separation prevention device is substantially cone shaped.

16. The tunneler device of claim 10, wherein the resilient separation prevention device is biased toward the non-deflected position when deflected inwardly towards the connecting device.

17. The tunneler device of claim 10, and wherein the free end of the resilient separation prevention device is biased outwardly from the connecting device when the connecting device is within the lumen of the catheter.

18. The tunneler device of claim 10, wherein the body of the connecting device defines a solid interior.

* * * * *

UNITED STATES PATENT AND TRADEMARK OFFICE
CERTIFICATE OF CORRECTION

| | |
|---|---|
| PATENT NO. | : 10,098,659 B2 |
| APPLICATION NO. | : 13/625253 |
| DATED | : October 16, 2018 |
| INVENTOR(S) | : Augustine |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1433 days.

Signed and Sealed this
Twenty-seventh Day of August, 2019

Andrei Iancu
*Director of the United States Patent and Trademark Office*